(12) United States Patent
Kaizik et al.

(10) Patent No.: US 6,403,836 B2
(45) Date of Patent: Jun. 11, 2002

(54) PROCESS FOR THE HYDROFORMYLATION OF OLEFINS BY REDUCING THE FORMIC ACID CONCENTRATION

(75) Inventors: Alfred Kaizik; Walter Toetsch, both of Marl; Wilfried Bueschken, Haltern; Felix Gosmann, Herten, all of (DE)

(73) Assignee: Oxeno Olefinchemie GmbH, Marl (DE)

( * ) Notice: Subject to any disclaimer, the term of this patent is extended or adjusted under 35 U.S.C. 154(b) by 2 days.

(21) Appl. No.: 09/789,571

(22) Filed: Feb. 22, 2001

(30) Foreign Application Priority Data

Feb. 26, 2000 (DE) .......................................... 100 09 207

(51) Int. Cl.$^7$ ................................................ C07C 45/50
(52) U.S. Cl. ...................... 568/451; 568/429; 568/449; 568/881; 568/885
(58) Field of Search ................................ 568/429, 449, 568/451, 881, 885

(56) References Cited

U.S. PATENT DOCUMENTS 5,321,168 A * 6/1994 Roussel et al. ............. 568/882

FOREIGN PATENT DOCUMENTS

| EP | 0011842 | * 11/1979 |
|----|---------|-----------|
| GB | 2 055 371 | 3/1981 |

* cited by examiner

Primary Examiner—Sreeni Padmanabhan
(74) Attorney, Agent, or Firm—Oblon, Spivak, McClelland, Maier & Neustadt, P.C.

(57) ABSTRACT

The present invention is a process for preparing $C_{4-25}$ aldehydes by hydroformylating the corresponding $C_{3-24}$ olefins in the presence of a cobalt hydroformylation catalyst, and catalytically decomposing the formic acid formed in the hydroformylation reaction or in the subsequent catalyst work-up. The aldehydes so produced may be hydrogenated to form alcohols.

27 Claims, No Drawings

PROCESS FOR THE HYDROFORMYLATION OF OLEFINS BY REDUCING THE FORMIC ACID CONCENTRATION

BACKGROUND OF THE INVENTION

1. Field of the Invention

The present invention relates to an improved process for the hydroformylation of olefins in the presence of unmodified cobalt carbonyl complexes, in which the concentration of formic acid in aqueous solutions containing cobalt compounds is reduced by catalytic decomposition.

2. Discussion of the Background

Higher alcohols, in particular those having from 4 to 25 carbon atoms, may be prepared by the catalytic hydroformylation (or oxo reaction) of olefins having one less carbon atom, followed by catalytic hydrogenation of the resulting aldehyde- and alcohol-containing reaction mixtures. These alcohols may be used, for example, in preparing plasticizers and detergents.

The type of catalyst system and the optimum reaction conditions for the hydroformylation depend on the reactivity of the olefin used. The dependence of the reactivity of the olefins on their structure is described, for example, by J. Falbe, New Syntheses with Carbon Monoxide, Springer-Verlag, Berlin, Heidelberg, N.Y., 1980, page 95 ff. In particular, the differing reactivity of isomeric octenes is known (B. L. Haymore, A van Hasselt, R. Beck, Annals of the New York Acad. Sci., 415 (1983), pages 159–175).

Industrial olefin mixtures which are used as starting materials for the oxo process comprise olefin isomers having a variety of structures, for example with different degrees of branching, different positions of the double bond in the molecule and possibly also different numbers of carbon atoms. This is particularly true of olefin mixtures which have been formed by dimerization or trimerization, or further oligomerization of $C_2$–$C_5$ olefins or other readily available higher olefins, or by cooligomerization of such olefins. For example, tripropenes and tetrapropenes and also dibutenes, tributenes and tetrabutenes are typical isomeric olefin mixtures which may be reacted by rhodium-catalyzed, or preferably cobalt-catalyzed hydroformylation reactions, to give the corresponding aldehyde and alcohol mixtures.

If alcohols having a very low degree of branching are desired, the hydroformylation reaction may preferably be carried out using unmodified cobalt catalysts. Compared to rhodium hydroformylation catalysts, cobalt hydroformylation catalysts provide higher yields of the particularly valuable oxo products having a higher content of straight chains.

The hydroformylation of olefins catalyzed by unmodified cobalt carbonyl complexes provides reaction mixtures comprising aldehydes, alcohols, their formic esters, unreacted olefins, free formic acid and additional by-products, as well as the catalyst. In order to obtain an almost cobalt-free reaction mixture suitable for further processing, the various cobalt compounds present in the hydroformylation product have to be removed. In addition, because the cobalt hydroformylation catalysts are expensive, any cobalt catalysts and catalysts residues which have been separated off should preferably be recycled.

During the hydroformylation and/or during removal of the cobalt compounds from the hydroformylation product, formic acid is formed by the hydrolysis of formic esters. The presence of formic acid inhibits the formation of active hydroformylation catalysts, for example, cobalt carbonyls, when the cobalt compounds of the hydroformylation product are regenerated to re-form active hydroformylation catalysts.

A conventional method for recovering the catalyst from the hydroformylation mixture comprises extracting cobalt compounds from the reactor output with an aqueous base, acidifying the extract to liberate $HCo(CO)_4$, and returning the $HCo(CO)_4$ to the hydroformylation reactor (Kuhlmann process). However, a disadvantage of this process is that one must dispose of the by-product salt of the base used to extract the cobalt compounds from the reactor output.

GB 2055371 describes a process comprising the following steps:

a) A portion of the cobalt carbonyls present in the hydroformylation product is reacted with an aqueous cobalt(II) salt solution to form $Co\{Co(CO)_4\}_2$. At the same time, the cobalt complex salt is extracted into the aqueous phase.

b) In a second step, the remaining cobalt carbonyls are oxidized with oxygen in the presence of an aqueous acid to give cobalt(II) salts. The aqueous extract thus formed is recycled to step a), above.

c) The active cobalt compounds, i.e. the cobalt hydroformylation catalyst, are prepared by reaction of the extract of step (a) with synthesis gas in the presence of an organic solvent.

A disadvantage of this process is that the separation of the cobalt compounds from the hydroformylation product, alone, requires an oxidation step and two phase separations.

WO 93/24437 describes a process for catalyst removal and regeneration, which essentially comprises the following steps:

a) After reducing the pressure of the hydroformylation output, the cobalt compounds are extracted with an aqueous solution having a pH of not more than 7, in particular an aqueous solution comprising formic acid, under either reductive conditions, or oxidative conditions (e.g., in the presence of oxygen).

If oxidative extraction conditions are employed, the following work-up procedure is used:

b) The aqueous extract comprising the cobalt compounds is concentrated by distillation. The top product (i.e., the lower density phase) is a mixture of water and acids (formic acid), part of which is recycled back to the extraction step a).

c) The aqueous concentrate from step b) is reacted with synthesis gas at elevated temperature at greater than atmospheric pressure to give a mixture comprising cobalt carbonyls.

d) The cobalt carbonyls are then stripped from the mixture obtained from step c). The remaining aqueous stream is recirculated back to step a).

e) The cobalt carbonyls are extracted from the stripping gas using the olefin starting material (for the hydroformylation).

In the nonoxidative work-up, the same process steps are carried out, but in a different order (a-d-c-b) and with the further difference that the largely cobalt-free aqueous stream from step d) is divided into two substreams which are recirculated to steps a) and b).

WO 93/24438 and U.S. Pat. No. 5,321,168 describe further developments of the process disclosed in WO 93/24437. In the same sequence of work-up steps, a palladium catalyst is additionally used for catalyst preformation (step c). In addition, U.S. Pat. No. 5,321,168 describes regenerating the activity of the palladium catalyst.

All of these work-up methods are very complex and incur high capital and operating costs.

An additional process is described in J. Falbe, New Syntheses with Carbon Monoxide, Springer-Verlag, Berlin, Heidelberg, N.Y., 1980, page 164, 165 (BASF process) and comprises the following steps:

a) Oxidation of the cobalt carbonyls by oxygen in the presence of acids, in particular formic acid formed in the process, to give cobalt(II) salts, followed by their extraction from the hydroformylation mixture.

b) Reduction of the cobalt(II) salts in the aqueous extract from step a) in the presence of an organic solvent to give cobalt carbonyls.

c) Extraction of the cobalt carbonyls into an organic phase, preferably the starting olefin, which is then fed into the hydroformylation reactor.

DE 196 54 340 describes a lower capital and operating cost hydroformylation process in which steps b) and c) are carried out in situ in the hydroformylation reactor. The space-time yields of this process also depend on the formation and stability of the catalyst complex in the hydroformylation reactor. The space-time yield may be further improved.

In all of the conventional processes described above, the formic acid concentration is established by the reaction conditions, and is generally neither influenced nor controlled at all, or is reduced by a further process step such as distillation.

It is therefore an object of the invention to develop a hydroformylation process for olefins which has a closed cobalt catalyst circuit which simplifies catalyst recirculation and provides for high space-time yields.

SUMMARY OF THE INVENTION

Applicants have surprisingly found that the space-time yield of a hydroformylation reaction can be increased if the formic acid concentration is reduced in either the aqueous cobalt(II) salt solution which is fed to the hydroformylation reactor, or in the over-all process.

The present invention accordingly provides a process for preparing aldehydes having from 4 to 25 carbon atoms by hydroformylation of the corresponding olefins having 3 to 24 carbon atoms in the presence of a cobalt catalyst, wherein the formic acid formed during the hydroformylation reaction, or in the subsequent catalyst work-up, is decomposed catalytically.

The decomposition of the formic acid is preferably carried out in an aqueous phase which is subsequently, i.e. after decomposition of the formic acid has occurred, returned in full or in part to the hydroformylation process.

The crude aldehydes prepared by the process of the present invention are preferably hydrogenated to form alcohols, which may be used in products such as plasticizers and detergents.

DETAILED DESCRIPTION OF THE INVENTION

The hydroformylation of olefins and the separation of the cobalt catalyst from the hydroformylation product can be carried out, for example, as described in DE 196 54 340 A1. This is a single-stage process in which the olefins are reacted with an aqueous cobalt salt solution and synthesis gas in a homogeneous phase, preferably in a cascaded reactor, particularly preferably by means of a mixing nozzle. The reaction product is subsequently treated oxidatively in the presence of an aqueous solution of carboxylic acids, predominantly formic acid. After phase separation, part of the aqueous phase comprising the cobalt salts is returned to the single-stage process and the organic phase is further treated to give the products (e.g., aldehydes) or hydrogenated to the corresponding alcohols. The aqueous solution recirculated to the hydroformylation reactor contains virtually the same amount of cobalt as is discharged with the hydroformylation mixture.

In principle, it is possible to catalytically decompose the formic acid in the hydroformylation reaction mixture, either before or after oxidation of the cobalt carbonyls. The cobalt compounds may then be separated from the hydroformylation product, afterward.

The process of the invention is preferably carried out by separating the components of the hydroformylation reaction mixture in the presence of an aqueous phase, by oxidative treatment of the hydroformylation reaction mixture and subsequent phase separation of the mixture into an organic product phase and an aqueous phase comprising cobalt salts and formic acid. All or part of the aqueous phase may be treated to catalytically decompose the formic acid. Any portion of aqueous phase in which the formic acid is not decomposed may be recycled back to the cobalt removal step. The largely formic acid free aqueous solution thus obtained can be recirculated back to the hydroformylation process.

In order to reduce the concentration of formic acid in the over all process, it may be sufficient to recycle back to the hydroformylation reactor only those portions of the aqueous phase in which the formic acid has been catalytically decomposed. Alternatively, it may be possible to reduce the concentration of formic acid in the over all process by decomposing only part of the formic acid in the decomposition reactor. In most cases, it is sufficient for at least 50%, preferably from 50 to 80%, of the formic acid formed in the process to be decomposed catalytically.

In any case, the solution or mixture which is treated to decompose the formic acid contains cobalt compounds, either as cobalt carbonyl or, after the oxidative work-up, as a cobalt(II) salt. The concentration of these cobalt compounds may vary within a wide range, as long as no cobalt compounds precipitate during the work-up. The concentration of the cobalt salt solution is partly determined by the amount of water which is discharged from the reactor with the hydroformylation mixture. Since water is discharged from the process with the essentially cobalt-free hydroformylation mixture (i.e. the organic phase after the catalyst has been separated off) it may be necessary to add water in order to avoid an increase in the cobalt compound concentration. The water may be added, for example, to the reactor feed, the cobalt removal unit or the crude product scrubber.

If desired, part of the formic acid may be separated off by distillation, and the formic acid in the distillate may be decomposed by the process of the present invention.

It is known that formic acid reacts with oxygen in the presence of heavy metal catalysts, in particular Pd catalysts, to form carbon dioxide and water. Likewise, formic acid can be oxidized in the absence of catalysts, e.g. using hydrogen peroxide.

Suitable formic acid decomposition catalysts used in the process of the present invention may comprise metals of groups VIII, VIIa and Ib of the Periodic Table of the Elements. These metals may be used in the form of the elemental metal or as metal oxides, in each case as a mixture of metals or as a mixed oxide. The catalyst may be supported on support materials including, for example, $Al_2O_3$, $SiO_2$, $TiO_2$, MgO and their mixed oxides, zeolites or activated carbon. In the process of the invention, supported catalysts, in particular $Pd/Al_2O_3$ catalysts, are preferred.

During the oxidative removal of formic acid in aqueous cobalt salt solutions, cobalt(II) is partly oxidized to cobalt (III), which may lead to precipitation of Co(III) compounds as the pH increases. When the decomposition of formic acid is carried out in the absence of oxygen or another oxidant, this reaction does not take place. For this reason, nonoxidative methods for decomposing formic acid are preferred, e.g. decomposition of the formic acid in the presence of synthesis gas, hydrogen, carbon monoxide, carbon dioxide or nitrogen.

In particular, the formic acid in aqueous cobalt salt solutions produced by the oxidative removal of cobalt from the hydroformylation product, can be decomposed catalytically.

The process of the present invention, in which formic acid is catalytically decomposed together with hydroformylation, may be carried out continuously or in a batch process, and either in the liquid phase or at least partly in the gas phase. Continuous decomposition in the liquid phase is the preferred method of carrying out the process.

The decomposition of formic acid can be carried out in stirred reactors or preferably in tube reactors. In tube reactors, the decomposition of formic acid can be carried out in a single pass or with recirculation of the solution (loop). The reactors may be operated as co-current reactors with trickle flow or with high liquid throughputs (pulse flow). It is also possible to connect a plurality of reactors together with one another. Each of these reactors may be operated in the same mode or in different modes.

The decomposition of formic acid is carried out in a temperature range from 100° C. to 300° C., preferably in the range from 120° C. to 200° C. The total pressure is generally from 1 bar to 350 bar, in particular from 1 bar to 25 bar.

The space velocities over the catalyst during the formic acid decomposition are from 0.5 $h^{-1}$ to 5 $h^{-1}$, in particular from 1 $h^{-1}$ to 3 $h^{-1}$.

If desired, the formic acid decomposition can be carried out in the presence of a purge gas, for example carbon monoxide, nitrogen, hydrogen or synthesis gas.

After concentration and premixing with starting material and possibly with synthesis gas, the aqueous solutions in which the concentration of formic acid has been reduced or eliminated entirely may be fed back into the hydroformylation reactor.

In another embodiment of the present invention, the catalytic decomposition of the formic acid is carried out in the presence of synthesis gas to form the cobalt catalyst used in the hydroformylation of the olefin starting materials (known as preformation).

The preparation of this cobalt catalyst ($HCo(CO)_4$ and $Co_2(CO)_8$) by reacting aqueous cobalt(II) salt solutions with synthesis gas at elevated pressures and temperatures is, as described above, known. This reaction may be accelerated by means of Pd catalysts, as is described in the patents U.S. Pat. No. 5,321,168, U.S. Pat. No. 5,434,318 and WO 93/24438. In the Pd catalyzed reactions, an aqueous cobalt (II) salt solution is reacted with synthesis gas over a Pd catalyst in the presence of an organic solvent, preferably an alcohol. A disadvantage of these methods is that the catalyst is deactivated and has to be periodically regenerated. The regeneration may be carried out as described, for example, in U.S. Pat. No. 5,321,168 by scrubbing the deactivated catalyst with water, with or without addition of formic acid, in the presence of synthesis gas at a pressure of 138–310 bar and a temperature of 120–170° C. According to the method described in U.S. Pat. No. 5,434,318, scrubbing is carried out under the above-mentioned conditions using a mixture of alcohol and aqueous formic acid.

The processes described above encompass only the formation of cobalt carbonyls from cobalt(II) salt solutions, but not the catalytic decomposition of formic acid.

In a particular embodiment of the present invention, the decomposition of formic acid can be carried out with simultaneous formation of cobalt carbonyl compounds, as either a batch or continuous process.

The combined reactions may be carried out in stirred reactors or preferably in tube reactors. If tube reactors are used, the reaction may be carried out in a single pass or with recirculation of the solution (loop). The tube reactors may be operated as co-current reactors with trickle flow or with high liquid throughputs (pulse flow). It is also possible for a plurality of reactors to be connected to one another. These reactors may be operated in the same mode or in different modes. The combined reactions may be carried out in the presence of synthesis gas at a total pressure of from 150 bar to 330 bar, in particular from 200 bar to 300 bar.

The molar ratio of carbon monoxide to hydrogen in the synthesis gas used in the combined catalyst synthesis and regeneration reactions can be in the range of from $2/1$ to $1/2$.

The reaction temperatures in the combined formic acid decomposition and preformation reactions may be in the range of from 140° C. to 220° C., preferably from 160° C. to 180° C. The space velocities over the catalyst (LHSV) are from 0.5 $h^{-1}$ to 5 $h^{-1}$, preferably from 1 $h^{-1}$ to 3 $h^{-1}$.

The same catalysts either for the decomposition of the formic acid alone, or for simultaneous decomposition of formic acid and formation of the cobalt catalyst.

The liquid reaction product from the combined decomposition and preformation reactor is introduced into the hydroformylation reactor. The waste gas obtained may be fed to the oxidizer, or preferably may be fed to the hydroformylation reactor.

If desired, the decomposition of the formic acid, together, if desired, with simultaneous formation of cobalt carbonyls, may be carried out in the presence of organic solvents comprising, for example, alcohols or aldehydes, in particular the starting materials and products of the hydroformylation reaction. These are preferably liquid hydrocarbons and/or the corresponding olefins which are liquid under the reaction conditions of the hydroformylation.

In any case, it is possible to recirculate the cobalt catalyst formed in the decomposition of formic acid to the hydroformylation reaction.

A hydroformylation plant operating according to the process of the present invention requires a somewhat higher capital investment compared to a conventional hydroformylation plant. This small capital cost disadvantage is more than compensated for by the higher space-time yield of the process of the present invention and also further advantages:

The formic acid concentration in the overall plant, in particular in the lower part of the hydroformylation reactor and in the downstream oxidizer (cobalt removal unit), is reduced.

The hydroformylation rate and thus the space-time yield of the hydroformylation reaction is increased, since the mean concentration of active cobalt compounds in the hydroformylation reactor is greater.

A further advantage is that the decomposition of the major part of the formic acid generated in the process results in the production of waste streams containing less formic acid. This reduces environmental pollution.

Having generally described this invention, a further understanding can be obtained by reference to certain specific examples which are provided herein for purposes of illustration only, and are not intended to be limiting unless otherwise specified.

EXAMPLE 1

A Co-containing process water (3850 g), obtained from the hydroformylation of dibutene after cobalt removal, which contains 0.85% by weight of Co (calculated as Co metal) as cobalt formate together with about 1.0% by weight of free formic acid, was treated in an intermediate-pressure circulation apparatus in the presence of 198 g of supported $Pd/Al_2O_3$ catalyst (1.0% by weight of $Pd/Al_2O_3$ extrudates, 4 mm×4 mm) at a temperature of 135° C. and a pressure of 15 bar to reduce the formic acid content. The change in the cobalt and formic acid concentrations and the pH of the Co process water over time were followed by appropriate sampling. The starting material and product analyses are shown in Table 1 below.

TABLE 1

Decomposition of formic acid in the presence of $Pd/Al_2O_3$ catalyst

| Residence time [min] | Formic acid [% by weight] | Cobalt content [% by weight] | pH |
|---|---|---|---|
| 0 | 1.0 | 0.85 | 3.45 |
| 5 | 0.65 | 0.85 | 3.82 |
| 10 | 0.47 | 0.84 | 4.01 |
| 15 | 0.32 | 0.85 | 4.22 |
| 20 | 0.22 | 0.84 | 4.45 |
| 30 | 0.10 | 0.85 | 4.81 |

As shown in Table 1, the concentration of free formic acid in Co process water can be reduced by catalytic decomposition, without oxygen, in the presence of Pd/Al2O3 catalyst.

The decrease in the formic acid concentration from 1.0% by weight to 0.10% by weight results in an increase in the pH from 3.45 to 4.81.

EXAMPLE 2

In a 2 liter high-pressure autoclave, the Co-containing process water of Example 1 was carbonylated before and after the formic acid decomposition described in Example 1 at 180° C. and 270 bar with synthesis gas (50% by volume of CO, 50% by volume of H2) to prepare cobalt carbonyls, i.e. a catalyst system active for hydroformylation of olefins. The Co process water contained 0.85% by weight of Co in the form of cobalt formate and 1.0 or 0.10% by weight of formic acid. After a treatment time of 3 hours, the carbonylation was stopped and the reaction product was analyzed to determine the cobalt carbonyl content. To determine the "active" cobalt in the Co water, the reaction product was reacted with iodine to liberate CO from the cobalt carbonyls. The amount of "active" cobalt is proportional to the amount of CO liberated.

After a treatment time of 3 hours, the formic acid-rich Co water had an activity of 21%, i.e. 21% of 0.85% by weight of Co is present as cobalt carbonyl, i.e. in a form which can be used as catalyst for the hydroformylation of olefins. In comparison, if Co-containing water having a low formic acid content, due to catalytic decomposition of formic acid, is used, a significantly higher activity of 38% of "active" cobalt is obtained.

EXAMPLE 3

Co-containing process water, obtained after removing cobalt from the hydroformylation of dibutene, containing 1.05% by weight of Co (calculated as Co metal) and about 0.95% by weight of free formic acid, was carbonylated at 180° C. and 270 bar with synthesis gas (50% by volume of CO, 50% by volume of $H_2$) in the presence of a supported $Pd/Al_2O_3$ catalyst (1.0% by weight of Pd) in powder form in a 2 liter high-pressure autoclave (1 l of Co water, 10 g of $Pd/Al_2O_3$) to prepare cobalt carbonyls, i.e. a catalyst system active for the hydroformylation of olefins. After a treatment time of 3 hours, the reaction was stopped and the reaction product was analyzed to determine the cobalt carbonyl content as described in Example 2. The analysis of the reaction product indicated an activity of about 40%.

This result shows that the reduction of the formic acid contents by catalytic decomposition and the Co carbonylation can be carried out in one process step.

EXAMPLE 4

The Co-containing water, carbonylated in Example 2 and containing 0.85% by weight of Co (total Co, calculated as metal) and-having a Co activity of 21%, was used as catalyst for the hydroformylation of dibutene ($C_8$-olefin mixture) to give $C_9$-aldehydes. The active cobalt carbonyls were first extracted from the stirred Co-containing process water, into the dibutene starting material (1000 g of dibutene, 250 g of Co water) in a 2 liter high-pressure autoclave. After separating off the aqueous phase, the dibutene laden with cobalt carbonyls was hydroformylated for 5 hours at a temperature of 185° C. and a synthesis gas pressure of 270 bar. After cooling to room temperature, the hydroformylation reaction mixture was depressurized and the cobalt catalyst extracted by treatment with acetic acid in air at 80° C. The reaction mixture was analyzed by gas chromatography (GC), and had the following composition: 10.5% by weight of $C_8$-olefins, 2.5% by weight of $C_8$-paraffins, 54.8% by weight of $C_9$-aldehyde, 22.6% by weight of $C_9$-alcohol, 4.5% by weight of $C_9$-formates and 5.1% by weight of high boilers. Accordingly, a dibutene conversion of 87.0% at a desired product selectivity of 90.6% was obtained, corresponding to a desired product yield of 78.8% based on the amount of dibutene used. $C_9$-aldehydes, $C_9$-alcohols and $C_9$-formates are considered to be the desired products.

EXAMPLE 5

For comparison with Example 4, the Co-containing process water carbonylated in Example 2, which had an increased Co activity of 38%, was used as a catalyst for the hydroformylation of dibutene to $C_9$-aldehyde. The active cobalt carbonyls were first extracted from the stirred Co-containing process water into the dibutene starting material (1000 g of dibutene, 250 g of Co water) in a 2 l high-pressure autoclave, as described in Example 4. After separating off the aqueous phase, the dibutene laden with cobalt catalyst was hydroformylated for 5 hours at 185° C. and a pressure of 270 bar. After cooling to room temperature, the reaction mixture was depressurized and the cobalt catalyst extracted by treatment with acetic acid and air at 80° C. The reaction mixture was analyzed by GC after the cobalt was removed indicates the following composition: 6.2% by weight of $C_8$-olefins, 3.3% by weight of $C_8$-paraffins, 55.1% by weight of $C_9$-aldehyde, 25.4% by weight of $C_9$-alcohol, 4.5% by weight of $C_9$-formates and 5.5% by weight of high boilers. Accordingly, a dibutene conversion of 92.3% at a desired product selectivity of 89.5% was obtained, corresponding to a desired product yield of 82.6% based on the dibutene used. $C_9$-aldehydes, $C_9$-alcohols and $C_9$-formates are considered to be the desired products.

Thus, a reduction in the formic acid content of the Co water leads to a significant improvement in the desired product yields and thus the space-time yield of the reaction.

The priority document of the present application, German patent application 10009207.1 filed Feb. 26, 2000, is incorporated herein by reference.

Obviously, numerous modifications and variations on the present invention are possible in light of the above teachings. It is therefore to be understood that within the scope of the appended claims, the invention may be practiced otherwise than as specifically described herein.

What is claimed as new and is intended to be secured by letters patent is:

1. A process for preparing aldehyde comprising:

hydroformylating a $C_{3-24}$ olefin in the presence of a cobalt hydroformylation catalyst to form a reaction mixture comprising a $C_{4-25}$ aldehyde, cobalt compounds, and formic acid; and decomposing the formic acid in the presence of a decomposition catalyst.

2. The process of claim 1, further comprising:

contacting the reaction mixture with an aqueous phase under oxidative conditions; and phase separating said reaction mixture and aqueous phase into an organic product phase and a cobalt-containing aqueous phase comprising cobalt salts and formic acid;

wherein all or part of the aqueous phase is contacted with a decomposition catalyst to decompose formic acid.

3. The process of claim 1, wherein said decomposing of the formic acid is carried out in an aqueous phase and all or part of said aqueous phase is subsequently returned to the hydroformylation process.

4. The process of claim 2, wherein said decomposing of the formic acid is carried out in an aqueous phase and all or part of said aqueous phase is subsequently returned to the hydroformylation process.

5. The process of claim 1, wherein said decomposition catalyst comprises a compound selected from the group consisting of a metal, mixed metal, metal oxide, and mixed metal oxide, and said metal or said metal of said metal oxide is a metal of groups I*b*, VII*a* and VIII of the Periodic Table of the Elements.

6. The process of claim 2, wherein said decomposition catalyst comprises a compound selected from the group consisting of a metal, mixed metal, metal oxide, and mixed metal oxide, and said metal or said metal of said metal oxide is a metal of groups I*b*, VII*a* and VIII of the Periodic Table of the Elements.

7. The process of claim 3, wherein said decomposition catalyst comprises a compound selected from the group consisting of a metal, mixed metal, metal oxide, and mixed metal oxide, and said metal or said metal of said metal oxide is a metal of groups I*b*, VII*a* and VIII of the Periodic Table of the Elements.

8. The process of claim 5, wherein said decomposition catalyst is supported on a support material comprising at least one support material selected from the group consisting of $Al_2O_3$, $SiO_2$, MgO, zeolites or activated carbon.

9. The process of claim 1 wherein said decomposing of formic acid is carried out continuously.

10. The process of claim 2, wherein said decomposing of formic acid is carried out continuously.

11. The process of claim 1, wherein said decomposing of formic acid is carried out at a temperature of from 100 to 300° C. and a pressure of from 1 to 350 bar.

12. The process of claim 2, wherein said decomposing of formic acid is carried out at a temperature of from 100 to 300° C. and a pressure of from 1 to 350 bar.

13. The process of claim 1, wherein at least 50% of the formic acid in said reaction mixture is catalytically decomposed.

14. The process of claim 2, wherein at least 50% of the formic acid in said reaction mixture is catalytically decomposed.

15. The process of claim 1, wherein said decomposing of formic acid is carried out in the presence of at least one gas selected from the group consisting of synthesis gas, hydrogen, nitrogen, and carbon monoxide.

16. The process of claim 2, wherein said decomposing of formic acid is carried out in the presence of at least one gas selected from the group consisting of synthesis gas, hydrogen, nitrogen, and carbon monoxide.

17. The process of claim 1, wherein said decomposing of formic acid is carried out in the presence of synthesis gas, thereby forming the cobalt hydroformylation catalyst.

18. The process of claim 2, wherein said decomposing of formic acid is carried out in the presence of synthesis gas, thereby forming the cobalt hydroformylation catalyst.

19. The process of claim 1, wherein said decomposing of formic acid is carried out at a pressure of from 150 to 330 bar.

20. The process of claim 2, wherein said decomposing of formic acid is carried out at a pressure of from 150 to 330 bar.

21. The process of claim 17, wherein said decomposing of formic acid is carried out at a temperature of from 140 to 220° C.

22. The process of claim 19, wherein said decomposing of formic acid is carried out at a temperature of from 140 to 220° C.

23. The process of claim 1, wherein said decomposing of formic acid is carried out in the presence of an organic solvent.

24. The process of claim 23, wherein said organic solvent comprises a hydrocarbon which is liquid under the reaction conditions of the hydroformylation and/or is a $C_{3-24}$ olefin.

25. The process of claim 23, wherein said organic solvent comprises said $C_{4-25}$ aldehyde and/or an alcohol obtained from the hydroformylation reaction.

26. The process of claim 17, wherein the cobalt hydroformylation catalyst formed during said decomposing of formic acid is recirculated to the hydroformylation reaction.

27. The process of claim 1, further comprising hydrogenating said $C_{4-25}$ aldehyde, thereby forming a $C_{4-25}$ alcohol.

* * * * *